(12) United States Patent
Duong

(10) Patent No.: US 8,029,502 B2
(45) Date of Patent: Oct. 4, 2011

(54) CRYOSURGICAL PROBE ASSEMBLY WITH MULTIPLE DEPLOYABLE CRYOPROBES

(75) Inventor: Thach Duong, Tustin, CA (US)

(73) Assignee: Endocare, Inc., Austin, TX (US)

( * ) Notice: Subject to any disclaimer, the term of this patent is extended or adjusted under 35 U.S.C. 154(b) by 784 days.

(21) Appl. No.: 11/430,323

(22) Filed: May 9, 2006

(65) Prior Publication Data

US 2006/0264920 A1 Nov. 23, 2006

Related U.S. Application Data

(60) Provisional application No. 60/683,515, filed on May 19, 2005.

(51) Int. Cl.
*A61B 18/02* (2006.01)
(52) U.S. Cl. .......................................... 606/21; 606/23
(58) Field of Classification Search .............. 606/20–26, 606/41
See application file for complete search history.

(56) References Cited

U.S. PATENT DOCUMENTS

| | | | |
|---|---|---|---|
| 5,683,384 A | 11/1997 | Gough | |
| 5,728,143 A | 3/1998 | Gough | |
| 5,800,484 A | 9/1998 | Gough | |
| 5,800,487 A | 9/1998 | Mikus | |
| 5,913,855 A | 6/1999 | Gough | |
| 5,993,444 A | 11/1999 | Ammar | |
| 6,016,452 A * | 1/2000 | Kasevich | 607/101 |
| 6,053,937 A * | 4/2000 | Edwards et al. | 607/104 |
| 6,074,412 A | 6/2000 | Mikus | |
| 6,231,570 B1 * | 5/2001 | Tu et al. | 606/41 |
| 6,500,175 B1 | 12/2002 | Gough | |
| 6,638,275 B1 * | 10/2003 | McGaffigan et al. | 606/41 |
| 6,706,037 B2 | 3/2004 | Zvuloni | |
| 6,767,346 B2 | 7/2004 | Damasco | |
| 7,204,833 B1 * | 4/2007 | Osorio et al. | 606/22 |
| 2002/0077628 A1 * | 6/2002 | Burbank et al. | 606/45 |
| 2003/0055415 A1 | 3/2003 | Yu | |
| 2004/0015162 A1 * | 1/2004 | McGaffigan | 606/34 |
| 2004/0049177 A1 * | 3/2004 | Zvuloni et al. | 606/21 |
| 2004/0082984 A1 * | 4/2004 | Osorio et al. | 607/105 |
| 2004/0220562 A1 * | 11/2004 | Garabedian et al. | 606/41 |
| 2004/0267248 A1 | 12/2004 | Duong | |
| 2005/0010200 A1 | 1/2005 | Damasco | |
| 2006/0122671 A1 * | 6/2006 | Albrecht et al. | 607/104 |

* cited by examiner

*Primary Examiner* — Michael Peffley
*Assistant Examiner* — Samantha Good
(74) *Attorney, Agent, or Firm* — Lawrence N. Ginsberg

(57) ABSTRACT

The cryosurgical probe assembly with multiple deployable cryoprobes includes a) a housing assembly; b) a plurality of elongated structural support elements, each securely connected at a first end to the housing assembly; c) a tip member securely connected to second ends of the plurality of elongated structural support elements, the tip member including a plurality of cryoprobe openings; and, d) a plurality of cryoprobes each having a shaft thereon, each shaft being deployable through a respective cryoprobe opening during operation to a deployed position used for ablating tissue. In an alternate embodiment, a cylindrical housing is utilized rather than elongated structural support elements.

14 Claims, 6 Drawing Sheets

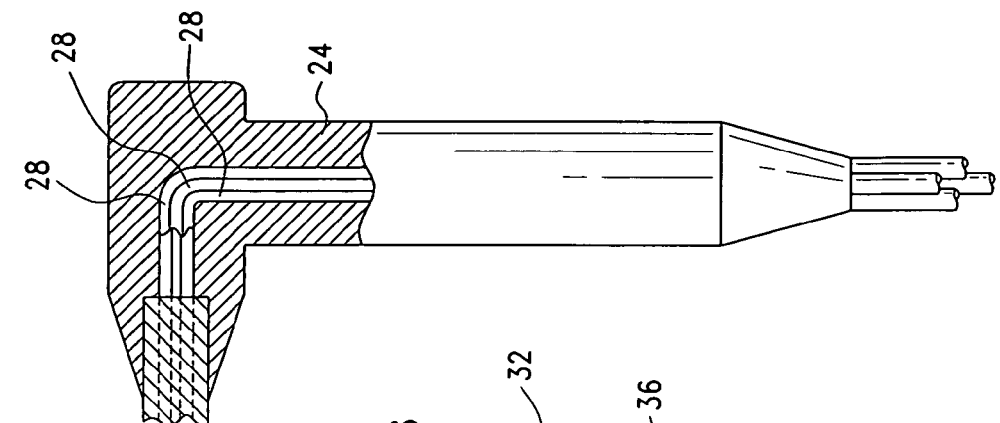
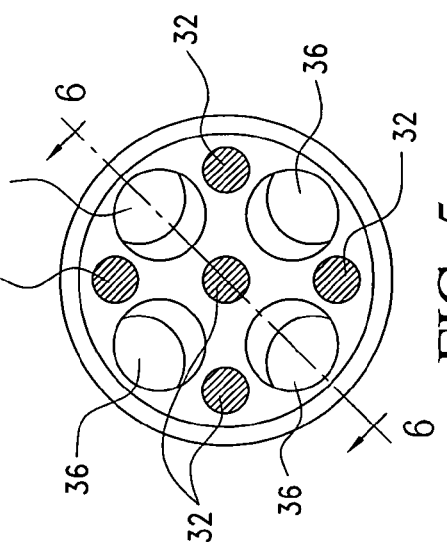
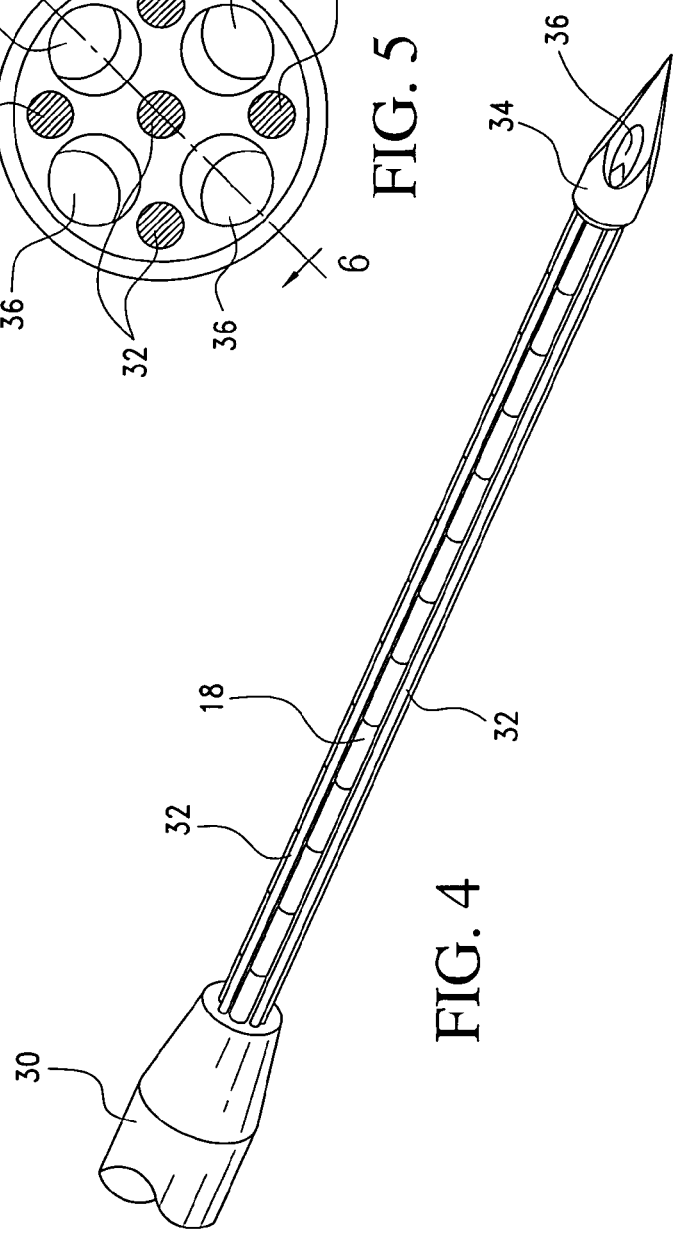

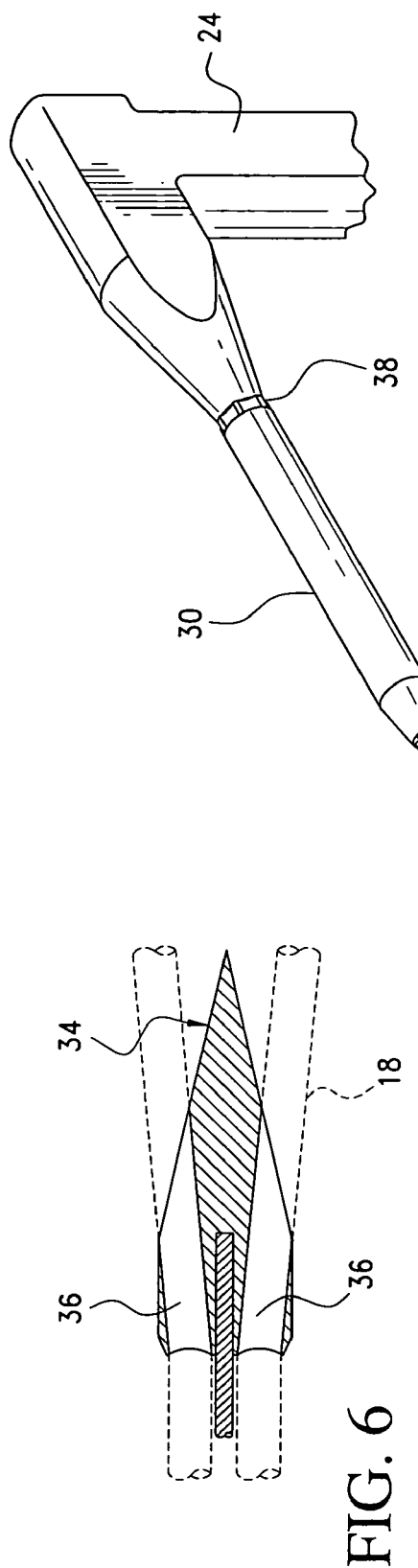
FIG. 6
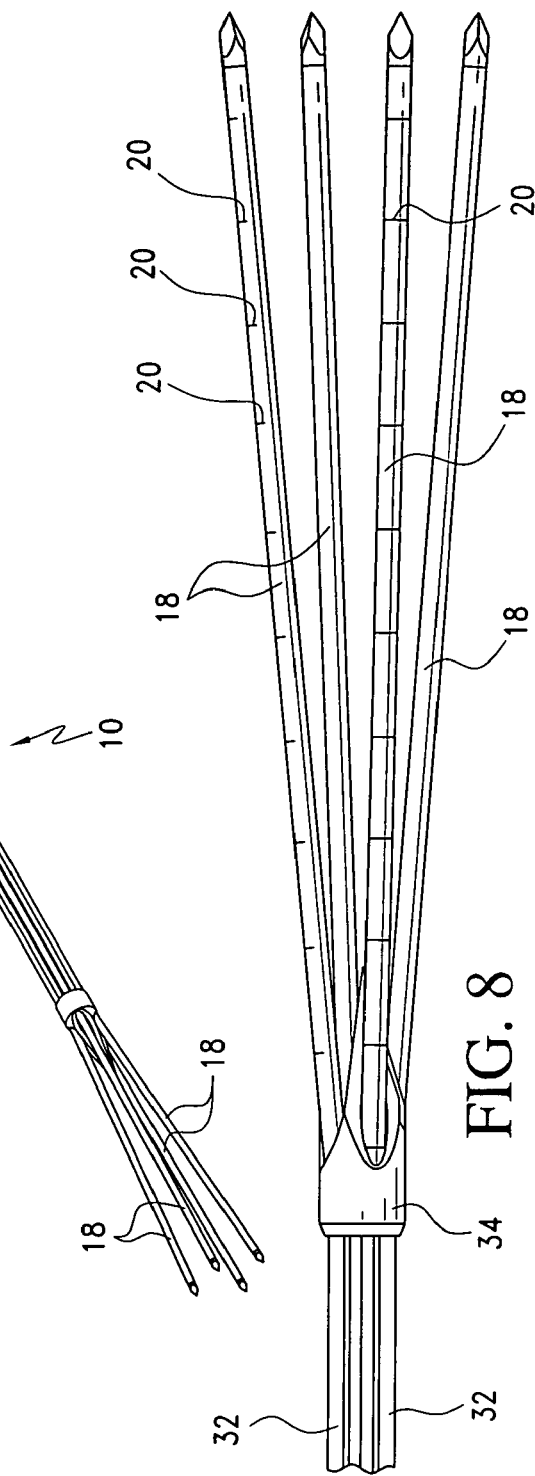
FIG. 7
FIG. 8

CRYOSURGICAL PROBE ASSEMBLY WITH MULTIPLE DEPLOYABLE CRYOPROBES

CROSS REFERENCE TO RELATED APPLICATIONS

This application is a nonprovisional application of, and claims the benefit of the filing date of, U.S. Prov. Pat. Appl. No. 60/683,515, entitled "CRYOSURGICAL PROBE ASSEMBLY WITH MULTIPLE DEPLOYABLE CRYOPROBES," filed May 19, 2005 by Thach Duong, the entire disclosure of which is incorporated herein by reference for all purposes.

BACKGROUND OF THE INVENTION

1. Field of the Invention

The present invention relates to cryosurgical probes and more particularly to a cryosurgical probe assembly that deploys multiple cryoprobes.

2. Description of the Related Art

Cryosurgery involving the use of a cryosurgical probe assemblies typically involves the use of cryoprobes that are each attached to a handle that are, in turn, connected to a high-pressure fluid line attached to a fluid source. Cryosurgical ablation of the prostate has generally required relatively small iceballs, i.e. 4 cm diameter by 6 cm length. For other applications, for example, renal applications, relatively larger iceballs are desired. Many other potential applications of cryosurgery may also require larger iceballs such as to ablate renal tumors, hepatic tumors, and pulmonary and thoracic tumors. Relatively large iceballs may also be required for palliative intervention.

U.S. Pat. No. 6,706,037, entitled "Multiple Cryoprobe Apparatus and Method," issued to Zvuloni et al., discloses a cryosurgery apparatus including an introducer having a hollow and a distal portion. The distal portion is sufficiently sharp so as to penetrate into a body. The hollow of the introducer is designed and constructed for containing a plurality of cryoprobes each of the cryoprobes being for effecting cryoablation, such that each of the plurality of cryoprobes is deployable through the distal portion of the introducer when the distal portion is positioned with respect to a tissue to be cryoablated. The introducer includes a heating and cooling device for pre-heating and pre-cooling gasses which are passed through at least a portion of the introducer and are subsequently delivered to at least one of the cryoprobes.

U.S. Pat. Publcn. No. 2004/0049177 also entitled "Cryoprobe Apparatus and Method," is a continuation of the '037 patent.

U.S. Pat. No. 5,913,855, entitled "Multiple Antenna Ablation Apparatus and Method", issued to E. J. Gough et al., discloses a multiple antenna device that includes a primary antenna with a lumen and a longitudinal axis, and a secondary antenna positionable in the lumen. At a selected tissue site the secondary antenna is deployed in a lateral direction relative to the longitudinal axis of the primary antenna. At least a portion of a distal end of the secondary antenna is structurally less rigid than the primary antenna. The primary antenna is constructed to be rigid enough to be introduced through tissue. A cable couples one or both of the antennas to an energy source. The multiple antenna device can be an RF antenna, a microwave antenna, a short wave antenna or the like.

U.S. Pat. No. 6,053,937, issued to S. D. Edwards et al., entitled "Multiple Electrode Ablation Apparatus and Method With Cooling Element," which is a continuation-in-part of the '855 case, discloses an ablation apparatus with an introducer including an introducer lumen, a proximal portion and a distal portion. Two or more electrodes are at least partially positioned in the introducer lumen. Each electrode is configured to be advanced from the introducer distal portion in a deployed state into a selected tissue site to define a volumetric ablation volume. A fluid delivery member is positioned on at least a portion of an exterior of one of the electrodes. The fluid delivery member is configured to be coupled to a fluid medium source. A cable is coupled to the electrodes.

Other patents related to the '855 and '937 patents include U.S. Pat. No. 5,683,384, entitled "Multiple Antenna Ablation Apparatus," U.S. Pat. No. 5,728,143, entitled "Multiple Antenna Ablation Apparatus and Method," U.S. Pat. No. 5,800,484, entitled "Multiple Antenna Ablation Apparatus with Expanded Electrodes," and U.S. Pat. No. 6,053,937, entitled "Multiple Electrode Ablation Apparatus and Method with Cooling Element." These all contain E. J. Gough as a co-inventor.

SUMMARY OF THE INVENTION

In a broad aspect, the present invention is embodied as a cryosurgical probe assembly with multiple deployable cryoprobes comprising: a) a housing assembly; b) a plurality of elongated structural support elements, each securely connected at a first end to the housing assembly; c) a tip member securely connected to second ends of the plurality of elongated structural support elements, the tip member including a plurality of cryoprobe openings; and, d) a plurality of cryoprobes each having a shaft thereon, each shaft being deployable through a respective cryoprobe opening during operation to a deployed position used for ablating tissue.

In another broad aspect, the cryosurgical probe assembly includes a cryoprobe subassembly and a support structure subassembly. The cryoprobe subassembly includes a housing assembly; and, a plurality of cryoprobes secured within the housing assembly, each cryoprobe including a shaft extending therefrom, each cryoprobe being connectable to a source of working fluid. The support structure subassembly includes an elongated handle; a plurality of elongated structural support elements, each securely connected at a first end to the handle; and, a tip member securely connected to second ends of the plurality of elongated structural support elements, the tip member including a plurality of cryoprobe openings. In a stowed position ends of the shafts of the cryoprobes do not extend beyond the tip member. During deployment the shafts are each directed through a respective cryoprobe opening to a deployed position used for ablating tissue.

In another broad aspect, the support structure subassembly of the cryosurgical probe assembly includes a cylindrical housing rather than elongated structural support elements.

Although the present invention may have many applications, as mentioned above, include ablation of renal tumors, hepatic tumors, and pulmonary and thoracic tumors. Relatively large iceballs may also be required for palliative intervention.

BRIEF DESCRIPTION OF THE DRAWINGS

FIG. 3 is a cross-sectional view of the cryosurgical assembly of FIG. 1.

FIG. 4 is an enlarged perspective view of the distal portion of the support structure subassembly of the FIG. 1 embodiment.

FIG. 5 is a view taken along line 5-5 of FIG. 2.

FIG. 6 is a cross-sectional view, taken along lines 6-6 of FIG. 5.

FIG. 7 shows this first embodiment in the fully deployed position.

FIG. 8 is an enlarged perspective view of the distal portion of the cryosurgical probe assembly in the fully deployed position.

The same elements or parts throughout the figures are designated by the same reference characters.

DETAILED DESCRIPTION OF THE INVENTION

Figure 1:
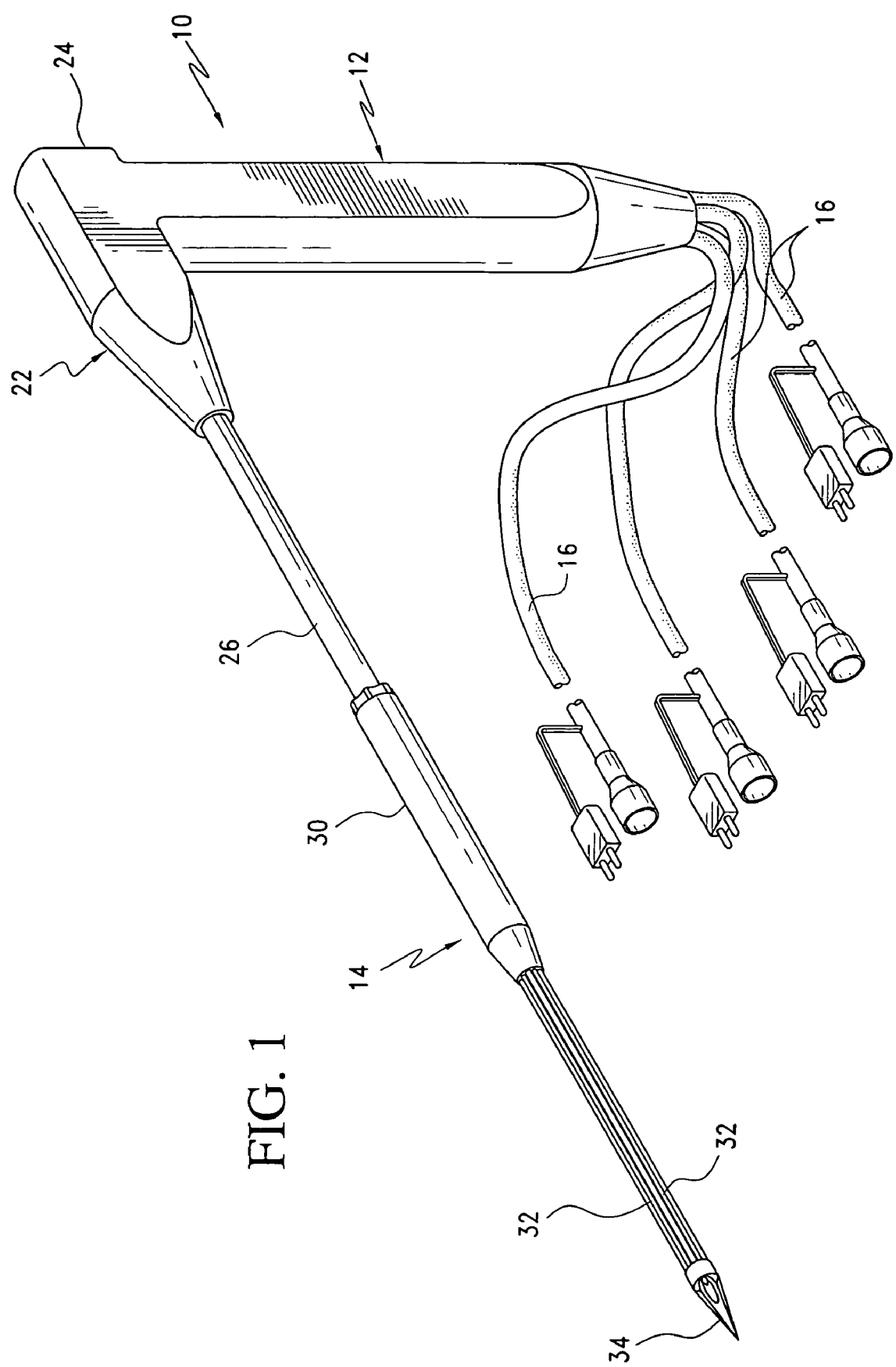
FIG. 1 is a perspective illustration of a first embodiment of the cryosurgical probe assembly of the present invention that utilizes a plurality of elongated structural support elements, shown in an undeployed position.
Figure 2:
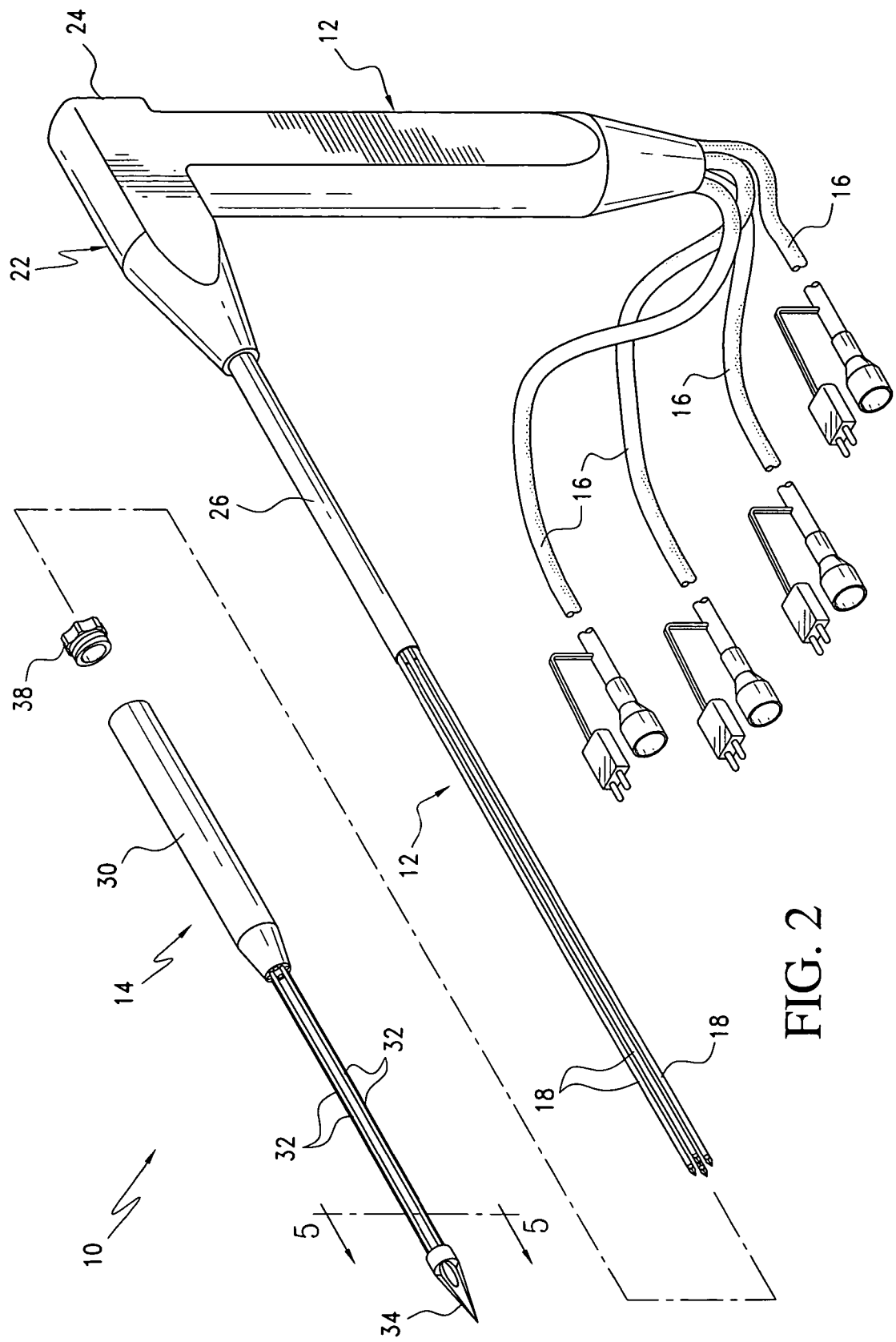
FIG. 2 is a perspective illustration of the FIG. 1 embodiment of the cryosurgical probe assembly shown with the support structure subassembly detached from the cryoprobe subassembly.

Referring now to the drawings and the characters of reference marked thereon, FIGS. 1-8 illustrate a first embodiment of the cryosurgical probe assembly of the present invention, designated generally as 10. The cryosurgical probe assembly 10 includes a cryoprobe subassembly, designated generally as 12 and a support structure subassembly, designated generally as 14. (These subassemblies are shown detached from each other in FIG. 2 for the purpose of clarity.) Each cryoprobe of the cryoprobe subassembly 14 includes a fluid supply line 16 that is connected at an inlet section to a source (not shown) of cryogenic fluid. The fluid source may be, for example, a cryosurgical system such as that manufactured by present assignee, Endocare, Inc., Irvine, Calif. Such a cryosurgical system typically utilizes argon gas from an argon gas source to provide Joule-Thomson cooling of the cryosurgical probes. Alternatively, nitrogen can be used. Alternatively, a fluid supply system can be utilized that does not require an external fluid supply source. Heating of the cryosurgical probes is typically provided by a helium gas source for providing a helium gas flow through the Joule-Thomson nozzle of the cryosurgical probe. This provides a heating effect. Such heating of the cryosurgical probes is provided to unstick the probes from the treated tissue for cryoprobe removal. Gas delivery assemblies of each cryoprobe subassembly 12 include a shaft 18 that has a freezing zone. Spaced markings 20 may be provided on the outer surface of the shaft 18, as can be seen in FIG. 8. These markings 20 may be, for example, at 1 cm intervals.

The cryoprobe subassembly includes a housing assembly, designated generally as 22. The housing assembly 22 includes a main housing 24 and a housing extension 26 extending from the main housing 24. The main housing 24 is shown as being L-shaped. This right angle is advantageous for many applications, including renal applications and interventional radiological applications.

Referring now to FIG. 3, it can be seen that multiple cryoprobes, each being designated generally as 28, are securely contained within the main housing 24 and housing extension 26 of the housing assembly 22. In a preferred embodiment each of the cryoprobes 28 is associated with an individual fluid supply line 16 to provide independent control. However, alternatively, the cryoprobes 28 may be connected via a single, shared supply line.

The support structure subassembly 14 includes an elongated handle 30. Five elongated structural support elements 32 are each securely connected at a first end to the handle 30. These structural support elements should be formed of a suitable strong material such as stainless steel.

A tip member 34 is securely connected to second ends of the elongated structural support elements 32. The tip member 34 includes four cryoprobe openings or channels 36 formed therein for accommodating shafts 18 of the various respective cryoprobes 28. Referring now to FIG. 6, it can be seen that the channels 36 are angled outwardly at a desired angle such that when the cryoprobes are deployed they are directed radially outwardly at this angle. The tip of the tip member 34 may be sharp as shown in, for example, FIG. 1; or, may be blunt or conical. The shape is dependent on the application, e.g. percutaneous or non-percutaneous. The tip member may have a diameter on the order of, for example, about 8 mm. Round iceballs can be created having diameters on the order of, for example, about 7 cm.

As illustrated in FIG. 1, in a stowed position ends of the shafts of the cryoprobes 18 do not extend beyond the tip member 34. However, during deployment, the shafts 18 are each directed through a respective cryoprobe opening 36 to the final deployed position used for ablating tissue, as shown in FIG. 7. To provide deployment, a wing nut 38 is loosened. An outer surface of the housing extension 26 is slideable within an inner surface of the elongated handle 30 to provide deployment of the cryoprobes 18. After the cryoprobes 28 are fully deployed, the wing nut 38 is then tightened down.

Figure 9:
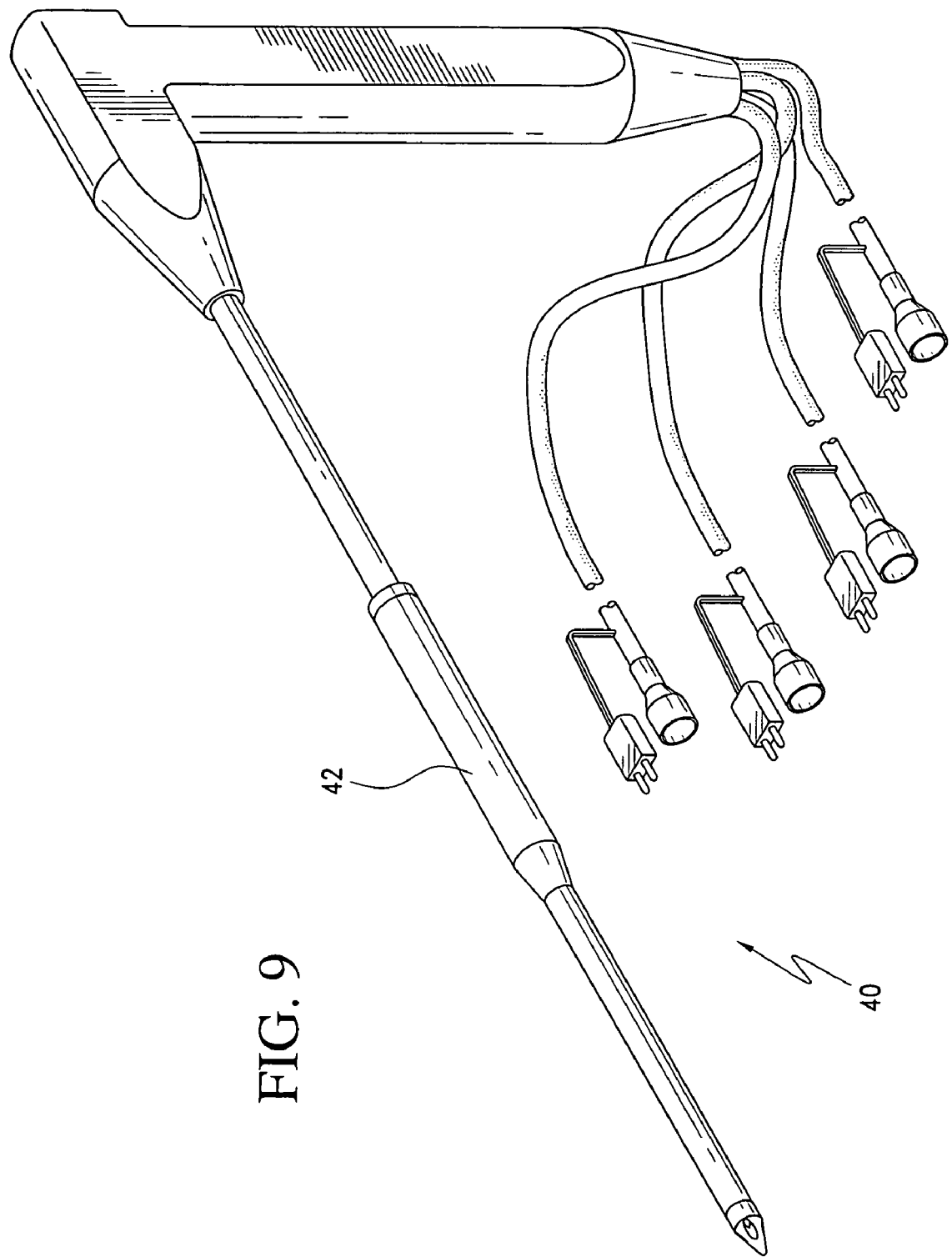
FIG. 9 is a perspective view of a second embodiment of the invention that uses an alternate support structure subassembly.
Figure 10:
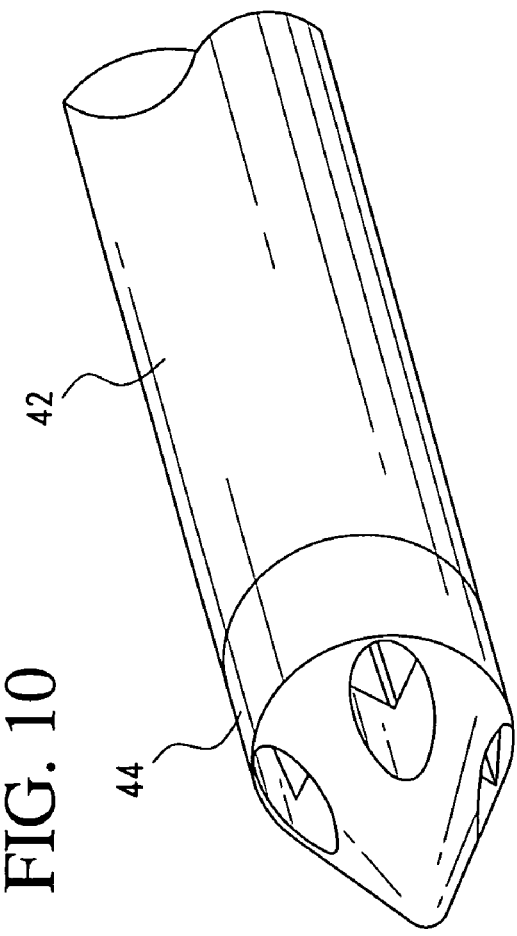
FIG. 10 is a perspective view of the distal portion of the cryosurgical probe assembly of FIG. 9 in a stowed position.
Figure 11:
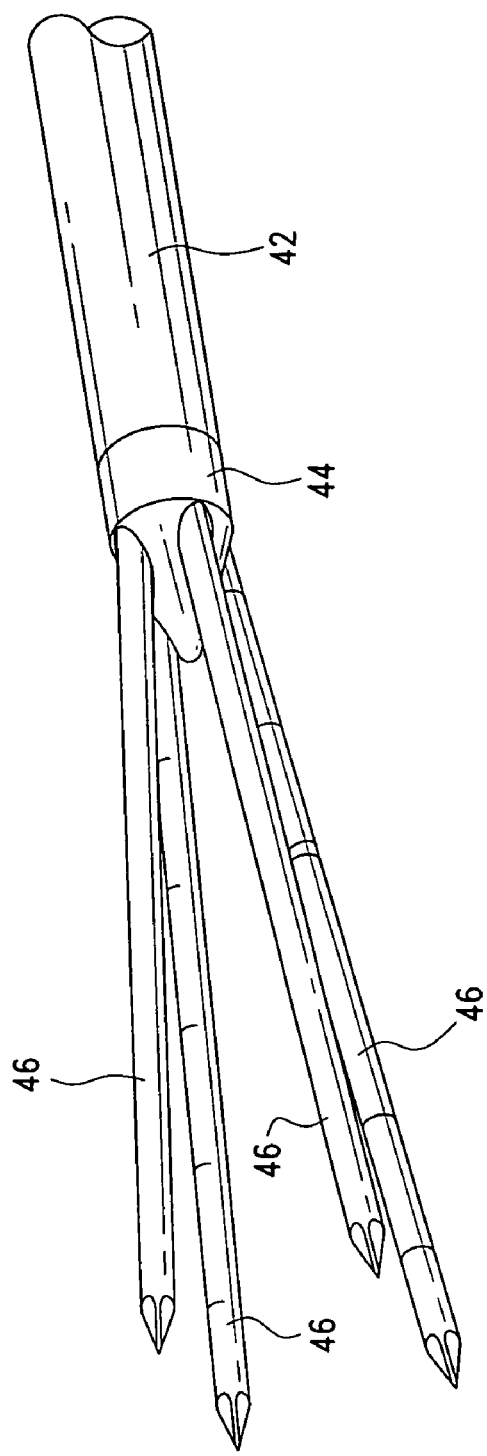
FIG. 11 shows this distal portion in a fully deployed position.

Referring now to FIGS. 9-11, a second embodiment of the cryosurgical probe assembly is illustrated, designated generally as 40. In this embodiment, the support structure subassembly includes a cylindrical housing 42 instead of the multiple elongated structural support elements of the first embodiment. As with the previous embodiment the tip member 44 may have a sharp end or a blunt, conical end. The cryoprobes 46 are directed out at an angle.

Although the internal construction of the cryoprobes has not been discussed in any detail herein such construction is known in the field. The cryoprobes may have a similar construction as cryoprobes presently manufactured by the present assignee, Endocare, Inc., Irvine, Calif. These may have similar components as cryoprobes described in U.S. Pat. Nos. 5,800,487 and 6,074,412, both entitled "Cryoprobe," issued to Mikus et al. and assigned to the present assignee that disclose cryoprobes using Joule-Thomson nozzles and finned tube helical coil heat exchangers. These patents are incorporated herein by reference, in their entireties.

A heat exchanger or cryostat is utilized to provide heat exchange between inlet gas and outlet gas. Although the heat exchanger is preferably a coiled fin tube heat exchanger various other types of heat exchangers may be utilized such as a tube-in-tube sintered cryostat, threaded cryostat, coiled/sintered cryostat, or stacked coil cryostat. These different types of cryostats are disclosed and claimed in U.S. Pat. Publication No. 20050010200 (U.S. Ser. No. 10/828,031), entitled Detachable Cryosurgical Probe, filed on Apr. 20, 2004, incorporated herein by reference in its entirety.

Cryoprobe internal construction is also described in U.S. Pat. Publication No. 20040267248 (U.S. Ser. No. 10/603,883), entitled Detachable Cryosurgical Probe, filed on Jun. 25, 2003, incorporated herein by reference in its entirety.

Certain applications may require guidance using various imaging techniques such as CT guidance, MRI or ultrasound.

Although the present invention has been discussed above with respect to a cryosurgical probe having a rigid outer sheath (shaft), the cryosurgical probe may be made to be malleable by including at least one malleable segment thereon. Malleable segments are formed of material that permit reshaping and bending to reposition the ablating surface for greater ablation precision. An example of a cryosurgical probe having malleable characteristics is disclosed and claimed in co-pending patent application Ser. No. 09/957,337, Pub. No. US 2003/0055415 A1, filed on Sep. 20, 2001 entitled Malleable Cryosurgical Probe, incorporated in its entirety herein by reference.

One method for providing malleable characteristics includes providing a malleable shaft with a bellows portion. U.S. Pat. No. 6,767,346, filed on Jul. 27, 2002 entitled Cryosurgical Probe with Bellows Shaft, incorporated in its entirety herein by reference, discloses use of a bellows portion for providing the necessary reshaping and bending.

If the cryosurgical probe is utilized in combination with ultrasound the outer sheath may have an echogenic coating with, for example, a porous microstructure having the ability to trap microscopic air bubbles. This creates thousands of highly efficient ultrasound reflectors on the surface of the sheath.

Thus, while the preferred embodiments of the devices and methods have been described in reference to the environment in which they were developed, they are merely illustrative of the principles of the invention.

Other embodiments and configurations may be devised without departing from the spirit of the invention and the scope of the appended claims.

The invention claimed is:

1. A cryosurgical probe assembly with multiple deployable cryoprobes, comprising:
   a) a housing assembly;
   b) a plurality of elongated structural support elements, each having a proximal end and a distal end, wherein the proximal ends of said plurality of elongated structural support elements is configured to be securely connected to said housing assembly, said plurality of elongated structural support elements comprising greater than two elongated structural support elements;
   c) a tip member configured to be securely connected to and supported by the distal ends of said plurality of elongated structural support elements, said tip member including a plurality of equally spaced, radially disposed cryoprobe openings and a sharp distal end; and,
   d) a plurality of cryoprobes each having a shaft thereon, each of said shafts being deployable through said respective cryoprobe opening during operation to a deployed position used for ablating tissue, said plurality of cryoprobes comprising greater than two cryoprobes, wherein each of said cryoprobe openings is elongated and extends through said tip member so as to provide guidance to each of said respective cryoprobes at a specific selected angle at a terminal end of said tip member; and wherein a proximal end of said tip member does not extend to a distal end of said housing assembly.

2. The cryosurgical probe system of claim 1, wherein said plurality of cryoprobes are radially spaced.

3. The cryosurgical probe system of claim 1, wherein said tip member comprises a conical distal end.

4. The cryosurgical probe system of claim 1, wherein said tip member comprises a sharp distal end.

5. The cryosurgical probe system of claim 1, wherein each said cryoprobe is individually controlled.

6. The cryosurgical probe system of claim 1, wherein said cryoprobe openings are each equally spaced from a distal end of said tip member.

7. A cryosurgical probe assembly with multiple deployable cryoprobes, comprising:
   a) a cryoprobe subassembly, comprising:
      i. a housing assembly; and,
      ii. a plurality of cryoprobes secured within said housing assembly, each cryoprobe including a shaft extending therefrom, said plurality of cryoprobes comprising greater than two cryoprobes, each of said cryoprobes being connectable to a source of working fluid;
   b) a support structure subassembly, comprising:
      i. an elongated handle;
      ii. a plurality of elongated structural support elements, each having a proximal end and a distal end, wherein the proximal ends of said plurality of elongated structural support elements is configured to be securely connected to said handle, said plurality of elongated structural support elements comprising greater than two elongated structural support elements; and,
      iii. a tip member configured to be securely connected to and supported by the distal ends of said plurality of elongated structural support elements, said tip member including a plurality of equally spaced, radially disposed cryoprobe openings, wherein each of said cryoprobe openings is elongated and extends through said tip member so as to provide guidance to each of said respective cryoprobes at a specific selected angle at a terminal end of said tip member wherein said tip member comprises a sharp distal end; and wherein a proximal end of said tip member does not extend to a distal end of said housing assembly, wherein 1) in a stowed position distal ends of said shafts of said cryoprobes do not extend beyond said tip member, and 2) during deployment said shafts are each directed through said respective cryoprobe opening to a deployed position used for ablating tissue.

8. The cryosurgical probe system of claim 7, wherein in said deployed position said cryoprobes are directed radially outwardly at said selected angle.

9. The cryosurgical probe system of claim 7, wherein said cryoprobe openings comprise channels being angled outwardly at said selected angle such that in said deployed position said cryoprobes are directed radially outwardly at said desired angle.

10. The cryosurgical probe system of claim 7, wherein said housing assembly comprises a main housing and a housing extension extending from said main housing.

11. The cryosurgical probe system of claim 7, wherein said housing assembly comprises a main housing and a housing extension extending from said main housing, an outer surface of said housing extension being slideable within an inner surface of said elongated handle to provide deployment of said cryoprobes.

12. The cryosurgical probe system of claim 7, wherein said housing assembly comprises a main housing and a housing extension extending from said main housing, said main housing being L-shaped.

13. The cryosurgical probe system of claim 7, wherein said plurality of cryoprobes comprises four radially spaced cryoprobes.

14. The cryosurgical probe system of claim 7, wherein said cryoprobe openings are each equally spaced from a distal end of said tip member.

* * * * *